United States Patent

Legay et al.

[11] Patent Number: 5,954,660
[45] Date of Patent: Sep. 21, 1999

[54] APPARATUS FOR FILTERING CARDIAC SIGNALS

[75] Inventors: Thierry Legay, Fontenay les Briis; Pascal Pons, Crolles; Luc Garcia, Saint Ismier, all of France

[73] Assignee: ELA Medical, S.A., Montrouge, France

[21] Appl. No.: 09/003,765

[22] Filed: Jan. 7, 1998

[30] Foreign Application Priority Data

Jan. 7, 1997 [FR] France .................................. 97 00065

[51] Int. Cl.⁶ .................................................. A61B 5/0402
[52] U.S. Cl. ............................................ 600/509; 128/902
[58] Field of Search .............................. 600/509; 128/902

[56] References Cited

U.S. PATENT DOCUMENTS 5,388,586  2/1995  Lee et al. .

FOREIGN PATENT DOCUMENTS 0 605 264  7/1994  European Pat. Off. ......... A61N 1/37

OTHER PUBLICATIONS

55091220, Patent Abstracts of Japan.
06325309 Patent Abstracts of Japan.

*Primary Examiner*—Scott M. Getzow
*Attorney, Agent, or Firm*—Orrick, Herrington & Sutcliffe LLP

[57] ABSTRACT

A device for filtering cardiac activity signals which receives input signals coming from collected physiological data, and delivers at an output, for processing data, signals spreading, in the frequency domain, over a widened spectral band. A first high-pass filter is used to reduce the extension of the spectral band of the signal received at the input. A compensation stage having a frequency characteristic (32) that is inverted as compared to that of the first high-pass filter is provided. The cut-off frequency (f1) of the first high-pass filter is greater than the low cut-off frequency (fo) of the spectral analysis band. Optionally, a second high-pass filter is provided, whose characteristic (38) presents a cut-off frequency corresponding to the low frequency (fo) of the spectral band. The high frequency of the spectral band may be similarly modified.

13 Claims, 3 Drawing Sheets

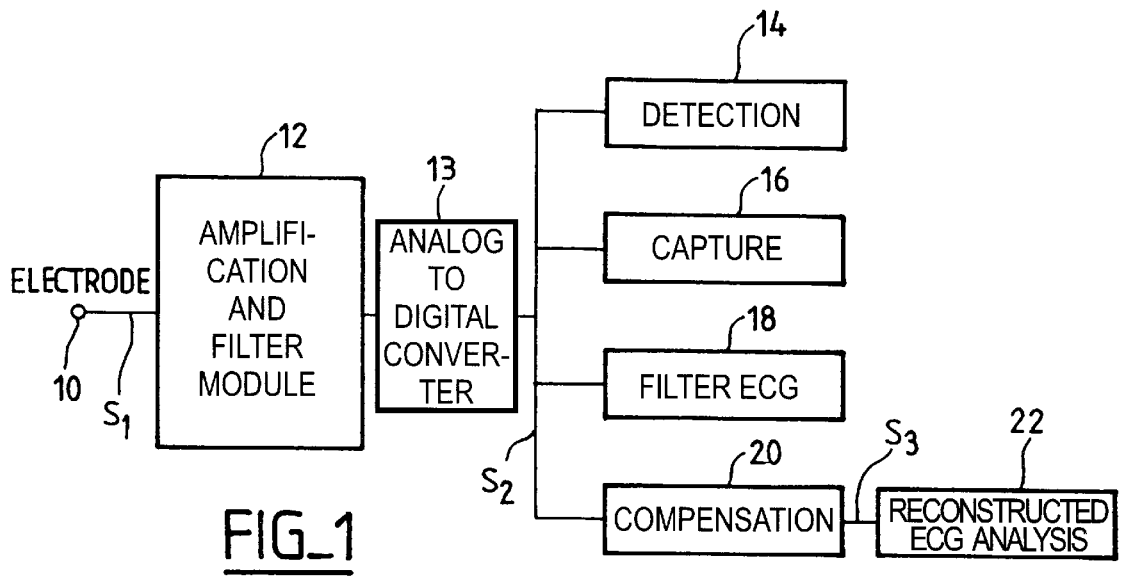
FIG_1
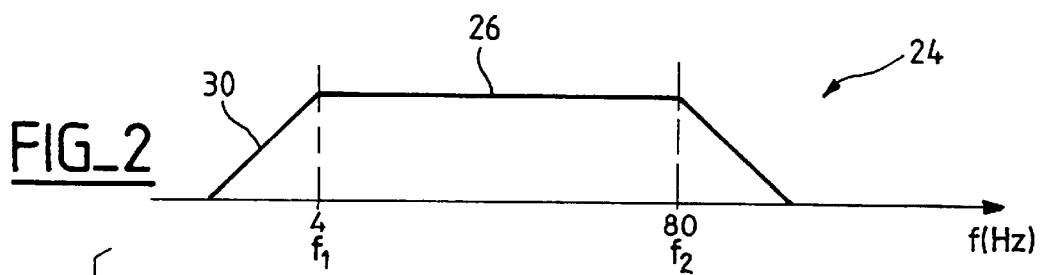
FIG_2
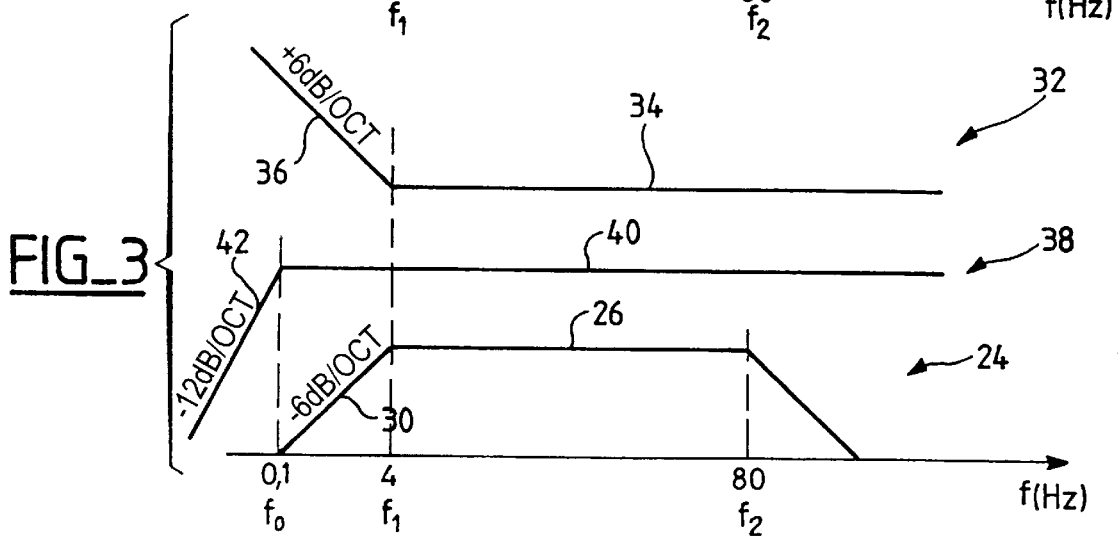
FIG_3
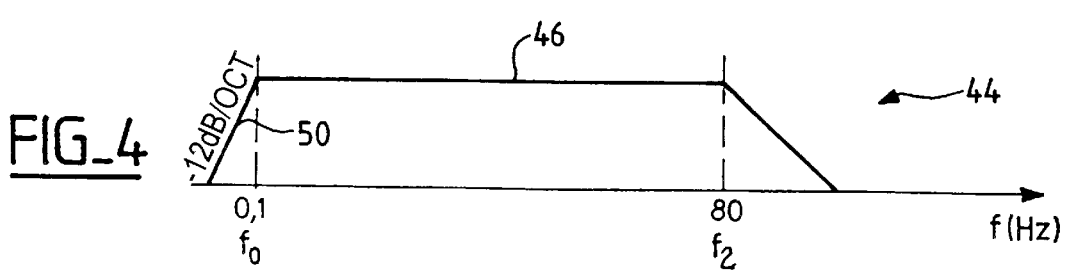
FIG_4

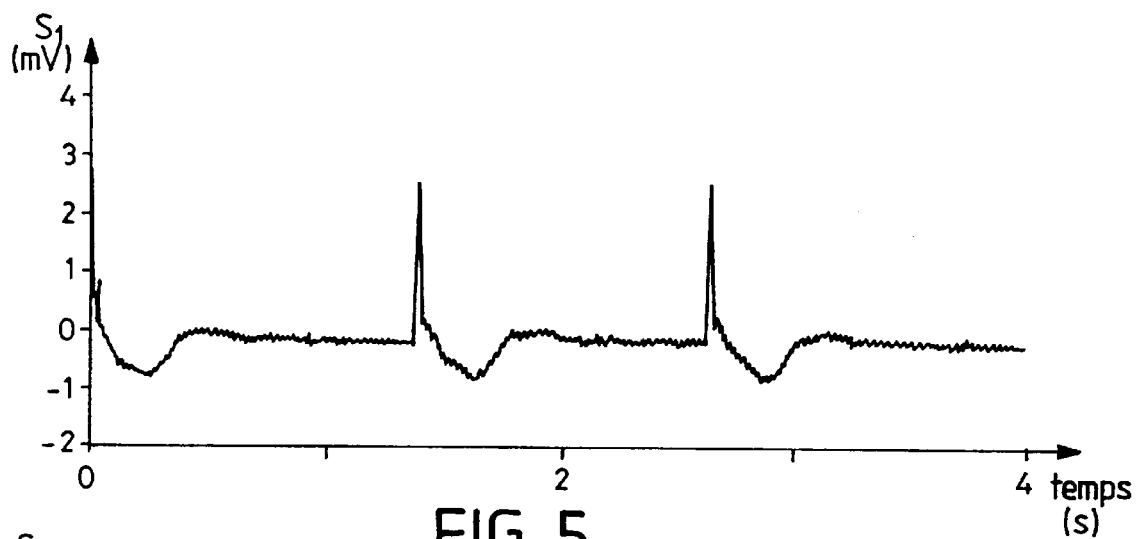
FIG_5
FIG_6
FIG_7

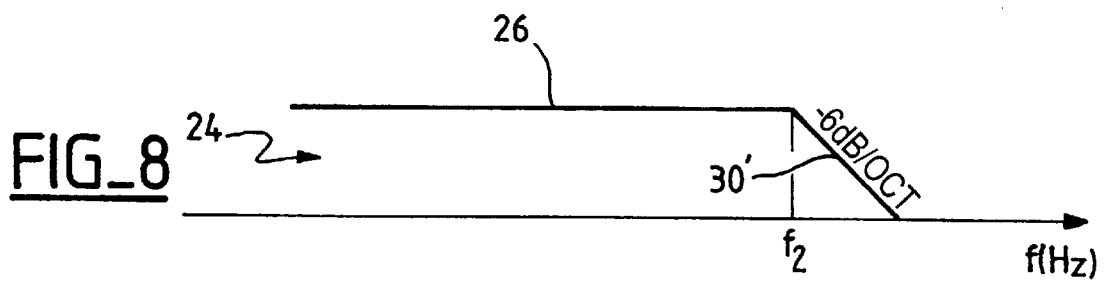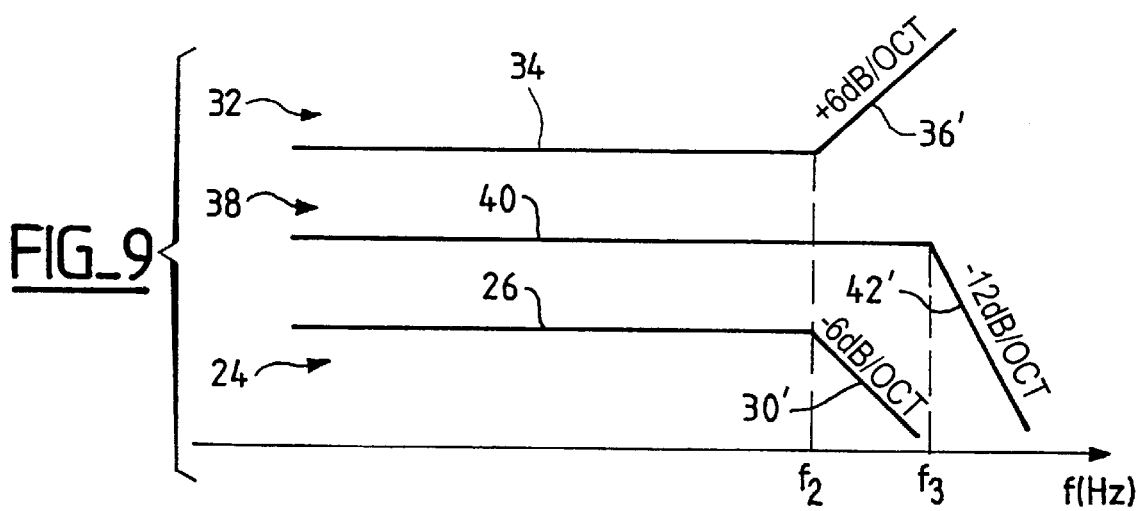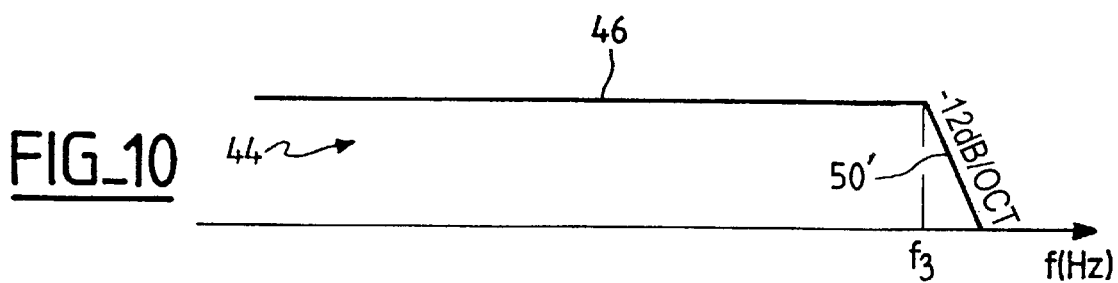

APPARATUS FOR FILTERING CARDIAC SIGNALS

FIELD OF THE INVENTION

The present invention concerns the processing of signals collected by medical devices, particularly by "active implantable medical devices" such those devices defined by the Jun. 20, 1990, Directive 90/385/EEC of the European Community Council, for example, cardiac pacemakers, defibrillators and/or cardiovertors, neurological devices, diffusion pumps for the distribution of medical substances and cochlear implants.

BACKGROUND OF THE INVENTION

The present invention will be mainly described in the context of an implementation of the invention for a cardiac pacemaker as an example. It should be understood, however, that the invention is applicable far more generally to a wide variety of active implantable medical devices and active medical devices which are not implantable devices, for example, devices carried externally by the patient. In these active medical devices, the cardiac activity is collected (sensed) at the input of electrodes and the obtained signal is applied to an amplification and filtering module.

The amplifier portion of the module is generally foreseen to receive signals having an amplitude on the order of a millivolt in a frequency band spreading over a range typically from 1 Hz to 80 Hz. However, the more recent devices detect signals outside these limits for processing. Indeed, for example, typical VDD pacemakers present lower sensitivities, on the order of 0.1 mV, because they use in the atrium a floating electrode for the collection of atrial depolarizations (P waves) and, to collect these signals, it is necessary to increase the gain of the amplifiers.

Furthermore, current pacemakers typically possess the so-called "Holter" functions, that is to say the memorization (storage) and analysis of the cardiac activity over a very long period, typically several hours. The analysis of the endocardiac signal that is operated to this aim necessitates a band-pass whose minimal (lower) frequency is far lower than the normal 1.0 Hz limit, typically 0.1 Hz, to be able, for example, to analyze the ST segment of the collected cardiac signal.

These improvements, however, entail the appearance of new problems, particularly due to the fact of the band-pass being larger in the low frequency domain.

First of all, independently of its sensitivity, the input amplifier has to be able to support the high amplitude of the stimulation pulse to be applied by the cardiac pacemaker device, which pulse amplitude can reach 10 V, and then to recover as fast as possible its capacity to detect (sensitivity) signals on the order a millivolt.

To be able to support the high voltage of the stimulation pulse, it is always foreseen to have a period of "blanking" (disconnection) of the input circuits at the moment when the pulse is delivered. Nevertheless, at the end of the blanking period, the moment when the amplifier of input is again commuted (connected) for collecting signals, a large saturation of the input stage can occur because the potential of the heart/electrode interface has not returned to its rest value.

This problem is further aggravated by the fact that the time of recovery of the amplifier becomes longer as the cut-off frequency of the high-pass filter of the input stage becomes lower. Thus, for a high-pass filter cut-off at 0.1 Hz, the recovery time of the amplifier is on the order of 10 s, which is totally incompatible with the need that one has to react rapidly to the changes in the detected cardiac signal.

It is indeed possible to apply the so-called technique of "pre-or post-charge", which concerns delivering electrical charges before or after the stimulation pulse to compensate for the lengthening of the recovery time. Nevertheless, this method is a large consumer of energy and would not be applied in a permanent manner without decreasing notably the duration of the life of the implanted device.

Another problem resides in the size of capacitor and resistor components, which increase as the cut-off frequency of the high-pass filter at the input stage is reduced. One sees that the more that the "listening" window widens in the low frequency domain (i.e., the frequency range used in the spectral analysis), it becomes necessary to have filter components of greater size, which is incompatible with the design imperatives of circuit miniaturization for implantable devices.

SUMMARY AND OBJECTS OF THE INVENTION

It is, therefore, an object of the invention to overcome the aforementioned disadvantages, by proposing a device that allows to widen particularly the spectral analysis band in the low frequency domain, without requiring components of great size and without affecting significatively the recovery time of the input amplifier of the pacemaker.

As one will understand, this problem is not limited only to cardiac pacemakers, but rather exists for each active medical device involving signals collected by collectors of a physiological parameter such as an activity collector, a respiration collector, etc., of which one wishes to be able to exploit subsequently a very low frequency component, while also having classic processing of the signal with reduced response times.

Broadly, the invention proposes to choose a cut-off frequency of the high-pass filter of the input stage of the pacemaker that is higher than the usual value (for example, 4 Hz instead of 1 Hz) and toresee a stage of compensation, preferably with digital filtering, that compensates for the attenuation due to the input high-pass filter.

Preferably, the compensation stage is used only when one desires to exploit very low frequency components of the collected (or collectable) signal.

The present invention can integrated in the implantable device or prosthesis (to allow, for example, an analysis in real time of the cardiac signal) or incorporated, for example, into a programmer or other external device designed for co-operation with an implanted device prosthesis (e.g., by telemetry) to process the collected signals. A further alternative is to incorporate the invention in an interface circuit that is interposed between the external programmer and a telemetry antenna.

One aspect of the invention is directed to a device which is a filtering device of the known type, receiving at its input signals from the means of collection of physiological data, and delivering at an output, to the means of processing the physiological data, the input signals spreading, in the frequency domain, over a widened spectral band, wherein the means of collection comprises a first high-pass filter reducing the width of the spectral band of the signal received at the input.

According to the invention, the filtering device also comprises a compensation stage comprising a means of accentuation with a frequency characteristic that is inverted as compared to that of the first high-pass filter, the cut-off frequency of the first high-pass filter being chosen to be greater than the low cut-off frequency of the widened spectral band.

In a preferred embodiment, the device also comprises a second high-pass filter, whose frequency characteristic presents a cut-off frequency corresponding to the low cut-off frequency of the widened spectral band.

In a preferred embodiment, the means of accentuation at he first high-pass filter have the same cut-off frequency and relatively inverted transfer functions (frequency characteristics).

Preferably, the transfer function of the second high-pass filter has an order that is greater than the order of the transfer function of the first high-pass filter.

In one embodiment, the low frequency of the widened spectral band is on the order 0.1 Hz and the cut-off frequency of the first high-pass filter is on the order 4 Hz.

The invention is equally applicable, in a symmetrical manner, to widening the frequency band at the high frequency end. This allows, particularly, to restrain the high end of the band-pass at stages of amplification and of digitization by limiting correlatively the influence of external high frequency signals able to cause saturation of the amplification stages, but in restoring subsequently, the useful signal in all of its spectral band width to allow a complete analysis.

In this last embodiment, the means of collection comprises a first low-pass filter reducing the extension of the spectral band of the received signal input and, according to the invention, the device comprises a compensation stage comprising a mean of accentuation with a frequency characteristic that is inverted as compared to that of the first low-pass filter, the cut-off frequency of the first low-pass filter being chosen to be lower than the high cut-off frequency of the widened spectral band.

In this aspect of the invention, the device preferably also comprises a second low-pass filter, whose characteristic presents a cut-off frequency corresponding to the high frequency of the widened spectral band.

In a preferred embodiment, the means of accentuation and the first low-pass filter have same cut-off frequency and relatively inverted transfer functions, and the order of the transfer function of the second low-pass filter is greater than the order of the transfer function of the first filter low-pass filter.

The filtering device of the invention, in one or the other of its forms of embodiment, can be incorporated in an active implantable medical device, or to an external programmer foreseen to co-operate with an implanted active medical device, or interface stage for a such programmer.

BRIEF DESCRIPTION OF THE DRAWINGS

Others characteristics, features, and advantages of the invention will appear to the reader of the following description of an exemplary of implementation of the invention, made with reference to the annexed drawings, in which like reference numerals refer to like elements, and in which:

FIG. 1 is a block diagram of the circuits for the collection and processing of the cardiac signal in accordance with a preferred embodiment of the invention;

FIG. 2 is a Bode diagram showing the frequency characteristic of attenuation of the filter at the input stage of implanted device;

FIG. 3 is a Bode diagram showing, respectively, the frequency characteristic of the filter at the input stage and the frequency characteristics of the filters according to the invention, FIG. 4 is a Bode diagram showing the resulting spectral response according to the invention;

FIGS. 5, 6 and 7 are trace recordings showing, respectively, the appearance of the endocardiac cardiac signal as collected, as filtered by the input stage of the pacemaker, and as reconstructed after application of the compensation stage according to the invention; and FIGS. 8, 9 and 10 are homologs of FIGS. 2, 3 and 4, in the case that one wishes to widen the spectral band in the high frequency domain.

DETAILED DESCRIPTION OF THE INVENTION

With reference to FIG. 1 an active implantable device is illustrated which, includes an electrode 10 collecting an endocardiac cardiac signal S1, that is applied to a circuit module 12 of amplification and filtering, then to an analogical to digital (A/D) converter 13. The A/D converter 13 has to have the necessary resolution to code the useful information of the signal S1 after attenuation by module 12.

The amplified, filtered and digitized signal S2 is directed to a plurality of modules, namely a module of detection 14, a module of capture 16, and a circuit 18 for the analysis of the electrocardiogram (ECG) filtered by the circuit module 12.

These modules can be specific circuits (that is, analog or digital hardware devices) or, in other embodiments, blocks of software instructions operating on a previously sampled and digitized signal inside of the module 12.

As indicated in the beginning of the description, current circuits, such the circuit 18 of analysis of the filtered ECG, operate on a spectral band spreading typically from 1 Hz to 80 Hz, these two frequencies corresponding to the high-pass and low- pass cut-off frequencies, respectively, of the filtering performed in the module 12.

As indicated in the beginning of the present description, most pacemaker circuits are not however adapted to the performances criteria of the most recent devices. Indeed, to realize Holter functions, it is necessary to be able to analyze the ECG signal in a listening window beginning at 0.1 Hz. But if one chooses for the high-pass filter at the input stage a very low cut-off frequency, the amplifier recovery time becomes prohibitive, which creates an incompatibility with the necessity to respond in a rapid manner to the succession of cardiac signals. In addition, a high-pass filter with a very low cut-off frequency requires capacitor and resistor components of relatively large size, which cannot be incorporated in a practicable implantable device.

To remedy to these difficulties, the invention proposes to raise the cut-off frequency of the high-pass filter of the module 12, for example, from 1 to 4 Hz, and to apply on the signal S2 an inverted corresponding compensation (block 20), to deliver a signal S3, which is a "reconstructed signal" spreading over a wide listening window in the low frequency domain, typically down to 0.1 Hz. It should be understood that the specific values provided herein are useful and exemplary and not limiting or restrictive of the scope of the invention.

The signal S3 is able to be analyzed by an appropriate module (block 22), insuring for example, an analysis of the ST segment that requires a band-pass of the ECG signal beginning at a frequency of 0.1 Hz.

In a first form of implementation, modules 20 and 22 are incorporated in the implanted device, in a manner to allow a study in real time, and by the implanted device, of the endocacardiac signal. In an alternate form of implementation, modules 20 and 22 are situated in an external programmer, for example, in the form of specific software routines of a cardiac signal analyzer, the digitized endocardiac signal being transmitted to the programmer by conventional and well-known telemetry techniques and circuits. In either or both forms, the device of compensation 20, like the high-pass filter of module 12, can be realized in an analog circuit form, by specific filtering circuits. But it can also, advantageously, be realized in a digital form, using discrete hardware or more preferably in the form of software routines performed by the pre-existing microprocessor of the device.

One is going now to explain more in detail the manner of operation of the compensation block 20. Referring to FIG. 2, the response curve (Bode diagram) of Module 12, whose frequency characteristic 24 presents a flat pass-bund portion 26 between two cut-off frequencies f1 and f2, with an attenuation at frequencies above f2 (low-pass function) and also an attenuation portion 30 at frequencies below f1 (the high-pass function).

The choice of the cut-off frequency f1 is a design compromise, mainly a function of size considerations of the components in module 12, but it is not critical. One will note, however, that the cut-off frequency f1, that is typically 4 Hz in the present invention, is particularly greater than of usual cut-off frequencies of high-pass filters of the prior art devices, which are on the order 1 Hz, and which advantageously allows one to reduce the size of the filter components.

The high cut-off frequency f2, that is not in fact principally concerned with this aspect of the invention, is typically on the order 80 Hz, and defines the high cut-off frequency of the listening window at the input.

The high-pass filter of module 12 is generally a filter of the first order, having for the characteristic portion 30 an attenuation of −6 dB/octave (one will see below that one can generalize this to larger orders).

Referring to FIG. 3, characteristic 24 of FIG. 2 is reproduced, to which one is going to apply compensations corresponding to characteristics 32 and 38, to give the reproduced band-pass 44 of FIG. 4.

To compensate for the attenuation 30 with the cut-off frequency at 4 Hz, one applies a compensation characteristic 32 with a flat response portion 34 at frequencies above f1=4 Hz, and a gain characteristic 36 for frequencies below f1. Ideally, the two characteristic cut-off frequencies are identical and equal to f1, but in practice one seeks to match them as best as possible so as to not generate distortions in the reconstituted signal. Preferably, for the gain one can use an amplification function of the first order, giving a slope of +6 dB/octave.

The combination of slopes of characteristics 30 and 36 gives, on the low frequency side of f1, a flat response, allowing therefore to restore the very low frequencies of the endocardiac signal.

One has thus reconstituted the spectral components that had been attenuated by the high-pass filter input of module 12.

The compensation portion 32 leads however to an infinite amplification for a null frequency, so that it is eminently unstable. To correct for this instability, one adds, in the stage of compensation 20, a high-pass filter whose characteristic 38 presents a flat response portion 40 above a cut-off frequency fo, for example, fo =0.1 Hz, and a progressive attenuation portion 42 on the low frequency side of the cut-off frequency fo. This second high-pass filter presents a function of stabilization of the compensation for the very low frequencies (below 0,1 Hz). This can be a filter of the first order (slope of −6 db/octave) but in this case the result of combining characteristics 32 and 38 would be to amplify equally the continuous component of the signal, particularly any residual gap (offset) voltage in output of module 12, before digitization by the block 13. This is why; to avoid having any gain on the continuous component, one preferably uses a filter characteristic portion 38 of the second order. The first order stabilizes the compensation characteristic 32 in the very low frequencies, and the second order cancels any the residual offset of module 12.

In the case of a second order filter, the two poles can be the same (as in the illustrated case, where one has a constant slope of −12 db/octave on the low side of cut-off frequency fo) or not the same, the two poles having, as indicated, distinct roles.

The solution of the present invention can be generalized to filters of greater order as follows. For a frequency characteristic 30 of n x −6 db/octave (high-pass filter of order n), the characteristic 36 will present a slope of n x +6 db/octave (filter of compensation of order n) and the characteristic 42 a slope of (n+1) x −6 db/octave (high-pass filter of order n+1) or, more generally, a slope of (n+k) x −6 db/octave, with k≧1 (high-pass filter of order n+k).

FIGS. 5 to 7 illustrate the effectiveness of a device of the present invention on an example of a collected ECG signal.

FIG. 5 corresponds to the collected signal S1 on the catheter (electrode) before the application of the high-pass filtering of module 12. FIG. 6 represents this same signal after application of the high-pass filtering of by module 12, for a first order high-pass filter at a cut-off frequency of 10 Hz, that is to say the signal S2: one sees particularly that the ST segment (after the main QRS peak) is particularly deformed and can not be analyzed suitably on the basis of this signal.

FIG. 7 illustrates the reconstructed signal S3, after application of the compensation stage according to the invention: if one compares S3 and S1, one sees that the reconstructed signal is extremely close to the original signal, and can therefore be analyzed in all aspects by the therapist or by an appropriate software analyzer.

The invention, as explained above, is equally applicable to the widening of the spectral band in the high frequency domain.

In FIGS. 8, 9 and 10, the frequency characteristics 24', 32', 38' and 44' shown as mirror images of the characteristics 24, 32, 38 ,and 44 shown in FIGS. 2, 3 and 4, considered in the high frequency domain of the Bode diagram, are represented.

Beyond a cut-off frequency f2, for example, f2=80 Hz, the frequency characteristic 26' of the input stage (FIG. 8) presents an attenuation 30' of −6 db/octave or, in a more general manner, n x −6 db/octave, n being the order of the corresponding low-pass filter.

FIG. 9 represents, at the high end the spectrum, the characteristic 32' of the stage that presents below cut-off frequency f2 a flat portion 34' and above f2 an accentuation 36' of +6 db/octave, or, in the general case, n x +6 db/octave.

The second low-pass filter presents a characteristic 38' with a flat portion 40' and an attenuation 42' above a cut-off frequency f3, chosen to be greater than cut-off frequency f2 (for example, a frequency f3=200 Hz), with a slope of −12 db/octave (or, in the general case, (n+1) x −6 db/octave) or, more generally, a slope of (n+k) x−6 db/octave, with k ≧ 1 (high-pass filter of order n+k).

This allows to insure, by analogy to what has been described above and by transposing the reasoning to the high frequencies, the stability of the system and the non-amplification of the residual noise in the output of module 12 beyond the cut-off frequency f3.

FIG. 10 illustrates the resulting band-pass 44' in the high frequency area, with a flat portion 46' up to the cutoff frequency f3 (typically, f3=200 Hz), allowing to restore significant spectral components situated particularly in the band 80–200 Hz, then a strong attenuation 50' at frequencies above f3, allowing one to attenuate non significant components of the signal, and particularly all the noise components.

Although the invention has been described in detail with reference to particular embodiments, it is to be understood that these embodiments and the component values provided are merely illustrative, and not limiting, of the principals of the invention, and that numerous other modifications may be made and other arrangements may be devised without departing from the spirit and scope of the present invention.

We claim:

1. A filtering device, having an input and an output, associated to a means for collecting physiological data signals, the filtering device input receiving signals (S1) issued from said means for collecting physiological data signals, and the filtering device output delivering signals (S3) to a means for processing physiological data signals, the delivered signals (S3) spreading, in the frequency domain, over a spectral band between a low cut-off frequency (fo) and a high cut-off frequency, wherein the improvement comprises the collection means comprising a first high-pass filter (12) having a first frequency characteristic (24) and a first cut-off frequency (f1); and a stage of compensation (20) comprising a means of accentuation having a second frequency characteristic (32) that is inverted as compared to the first frequency characteristic of the first high-pass filter, wherein the first cut-off (f1) frequency of the first high-pass filter is greater than the low cut-off frequency (fo) of the spectral band.

2. The device of claim 1, further comprising a second high-pass filter characteristic (38) presenting a second cut-off frequency corresponding to the low cut-off frequency (fo) of the spectral band.

3. The device of claim 2, in which the second high-pass filter further comprises an order and the transfer function of the first high-pass filter further comprises an order, and the order of the second high-pass filter transfer function is greater than the order of the first high-pass filter.

4. The device of claim 1, in which the mean of accentuation and the first high-pass filter have same cut-off frequency (f1) and relatively inverted transfer functions.

5. The device of claim 1, in which the low cut-off frequency (fo) of the spectral band is on the order of 0.1 Hz.

6. The device of the claim 1, in which the first cut-off frequency (f1) of the first high-pass filter is on the order of 4 Hz.

7. A filtering device having an input an output, associated to a means for collecting physiological data signals, the filtering device input receiving signals from said means for collecting physiological data signals, and the filtering device output delivering signals (S1) to a means for processing physiological data signals, the delivered signals spreading, in the frequency domain, over a spectral band between a low cut-off frequency and a high cut-off frequency, wherein the improvement comprises the means for collection further comprising a first low-pass filter having a first frequency characteristic (24') and a first cut-off frequency; and a stage of compensation comprising a means of accentuation having a second frequency characteristic (32') inverted as compared to the first frequency characteristic of the first low-pass filter, wherein the first cut-off frequency of the first low-pass filter is less than the high cut-off frequency (f3) of the spectral band.

8. The device of claim 7, further comprising a second low-pass filter, having a second filter characteristic (38') and a second cut-off frequency corresponding to the high cut-off frequency of the spectral band.

9. The device of claim 8, in which the the second low-pass filter has a transfer function order and the first low pass filter has a transfer function order and the transfer function order of the second low-pass filter is greater than the transfer function order of the first low-pass filter.

10. The device of claim 7, in which the means of accentuation further comprises a cut-off frequency and accentuation means cut-off frequency and the first low-pass filter first cut-off frequency further comprise same cut-off frequency and relatively inverted transfer functions.

11. An active implantable medical device comprising a means for collecting physiological data signals and the filter device of any of claims 1–10.

12. An external programmer co-operating with an active implanted medical device having a means for collecting physiological data and comprising the filter device of any of claims 1–10.

13. An interface circuit for an external programmer co-operating with an active implanted medical device having a means for collecting physiological data signals, said interface circuit incorporating the filter device of any of claims 1–10 and being interposable between said external programmer and said active implantable medical device.

* * * * *

UNITED STATES PATENT AND TRADEMARK OFFICE
CERTIFICATE OF CORRECTION

PATENT NO.   : 5,954,660
DATED        : September 21, 1999
INVENTOR(S)  : Legay et al.

It is certified that error appears in the above-identified patent and that said Letters Patent is hereby corrected as shown below:

Column 1,
Line 53, delete "order a" and insert -- order of a -- therefor;

Column 2,
Line 11, delete "increase as" and insert -- increases -- therefor;
Line 27, delete "significatively" and insert -- significantly -- therefor;
Line 32, delete "physicological" and insert -- physiological -- therefor;
Line 40, delete "foresee" and insert -- to foresee -- therefor;
Line 46, delete "can integrated" and insert -- can be integrated -- therefor;

Column 3,
Line 31, delete "mean" and insert -- means -- therefor;
Line 50, delete "for a such" and insert -- for such a -- therefor;

Column 4,
Line 32, delete "such the" and insert -- such as the -- therefor;
Line 49, delete "remedy to" and insert -- remedy -- therefor;

Column 5,
Line 26, delete "than of" and insert -- than -- therefor;
Line 33, delete "order" and insert -- order of -- therefor;

Column 6,
Line 13, delete "cancels any" and insert -- cancels -- therefor;
Line 33, delete "filtering of" and insert -- filtering -- therefor;

Column 7,
Line 52, delete "have same" and insert -- have the same -- therefor;

Column 8,
Line 3, delete "of the claim" and insert -- of claim -- therefor.
Line 6, delete "input an" and insert -- input and -- therefor;
Line 29, delete "low pass" and insert -- low-pass -- therefor;

UNITED STATES PATENT AND TRADEMARK OFFICE
CERTIFICATE OF CORRECTION

PATENT NO. : 5,954,660
DATED : September 21, 1999
INVENTOR(S) : Legay et al.

It is certified that error appears in the above-identified patent and that said Letters Patent is hereby corrected as shown below:

<u>Column 8, (cont'd),</u>
Line 35, delete "comprises" and insert -- comprise -- therefor; and
Line 37, delete "comprise" and insert -- comprises the -- therefor.

Signed and Sealed this

Twenty-first Day of June, 2005

JON W. DUDAS
*Director of the United States Patent and Trademark Office*